(12) United States Patent
Murray

(10) Patent No.: US 8,500,707 B2
(45) Date of Patent: Aug. 6, 2013

(54) DRAINABLE POUCH WITH POCKET FOR DRAIN CHUTE

(75) Inventor: Kimberly Murray, Pittsburgh, PA (US)

(73) Assignee: Convatec Technologies Inc., Las Vegas, NV (US)

( * ) Notice: Subject to any disclaimer, the term of this patent is extended or adjusted under 35 U.S.C. 154(b) by 11 days.

(21) Appl. No.: 12/936,249

(22) PCT Filed: Apr. 7, 2009

(86) PCT No.: PCT/US2009/039759
§ 371 (c)(1),
(2), (4) Date: Oct. 4, 2010

(87) PCT Pub. No.: WO2010/077377
PCT Pub. Date: Jul. 8, 2010

(65) Prior Publication Data
US 2011/0028923 A1   Feb. 3, 2011

(51) Int. Cl.
*A61F 5/44* (2006.01)
*A61F 5/445* (2006.01)
*B65D 33/01* (2006.01)
*B65D 33/16* (2006.01)
*B65D 33/24* (2006.01)

(52) U.S. Cl.
USPC ........... 604/332; 604/277; 604/322; 604/326; 604/327; 604/337; 604/339; 383/210.01; 383/50; 383/57; 383/58; 383/61.1; 383/62; 383/67; 383/77; 383/78; 383/82; 383/83; 383/84; 383/85; 383/86.2; 383/88; 383/89; 383/90; 383/91; 383/98; 383/99; 383/123; 383/126; 222/111; 222/182; 222/527; 222/528; 222/530; 222/538; 222/539

(58) Field of Classification Search
USPC ............... 604/322–327, 385.04, 385.19, 408; 383/14, 210.1, 50, 57, 58, 61.1, 62, 67, 77, 383/78, 82, 83, 847, 85, 86.2, 88, 89, 90, 383/91, 98, 99, 123, 126; 222/111, 182, 222/499, 527, 528, 530, 538, 539; 4/144.2, 4/144.3
See application file for complete search history.

(56) References Cited

U.S. PATENT DOCUMENTS

| | | | |
|---|---|---|---|
| 2,520,831 A * | 8/1950 | Chincholl | 604/335 |
| 3,825,005 A | 7/1974 | Fenton | |
| 4,519,797 A | 5/1985 | Hall | |
| 4,676,851 A | 6/1987 | Scheibner | |
| 4,691,371 A * | 9/1987 | Derby | 383/62 |
| 5,030,013 A * | 7/1991 | Kramer | 383/61.1 |
| 5,248,308 A | 9/1993 | Von Emster | |
| 5,676,466 A | 10/1997 | Lindenbeck | |
| 5,863,131 A * | 1/1999 | Nakamura | 383/89 |
| 5,968,023 A * | 10/1999 | Olsen | 604/334 |
| 6,589,221 B1 | 7/2003 | Andersen et al. | |
| 6,726,667 B2 | 4/2004 | Leise | |
| 6,780,172 B2 | 8/2004 | Andersen et al. | |

(Continued)

*Primary Examiner* — Melanie Hand
*Assistant Examiner* — Joshua Lee

(57) ABSTRACT

A drainable ostomy pouch includes a collection portion and a drain chute extending from the collection portion having a discharge opening for permitting emptying of contents from the pouch. The drain chute is foldable between an open condition in which the drain chute is extended from the collection portion, and a closed condition in which the drain chute is folded towards the collection portion; and a pocket for receiving at least a portion of the drain chute when the drain chute is in its closed condition.

11 Claims, 14 Drawing Sheets

U.S. PATENT DOCUMENTS

| | | |
|---|---|---|
| 6,887,222 B2 | 5/2005 | Mandzij |
| 7,306,581 B2 | 12/2007 | Breakwell et al. |
| 7,842,018 B2 * | 11/2010 | Schena et al. ............. 604/344 |
| 7,879,016 B2 * | 2/2011 | Mandzij et al. ............ 604/335 |
| 7,947,025 B2 * | 5/2011 | Buglino et al. ............ 604/335 |
| 2003/0028160 A1 * | 2/2003 | Leise et al. ............... 604/334 |
| 2003/0167042 A1 * | 9/2003 | Poulsen .................... 604/327 |
| 2004/0049837 A1 * | 3/2004 | Falconer et al. ............. 4/144.1 |
| 2005/0131360 A1 | 6/2005 | Winther et al. |
| 2006/0111682 A1 * | 5/2006 | Schena et al. ............. 604/334 |
| 2008/0051743 A1 | 2/2008 | Falconer |
| 2009/0034882 A1 * | 2/2009 | Chih et al. ..................... 383/2 |
| 2011/0028923 A1 | 2/2011 | Murray |

* cited by examiner

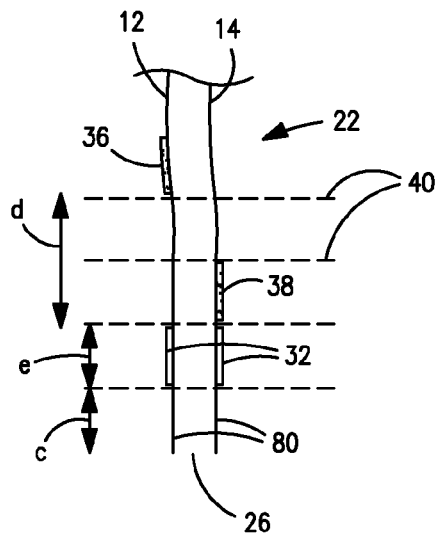
FIG. 16
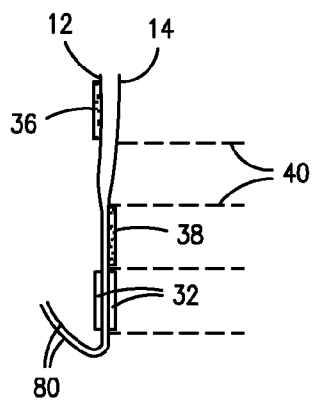 
FIG. 17a         FIG. 17b
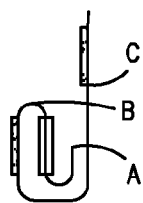 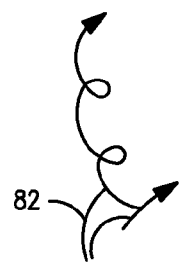
FIG. 17c         FIG. 17d

DRAINABLE POUCH WITH POCKET FOR DRAIN CHUTE

CROSS REFERENCE

This patent application claims the benefit of International Application Serial No. PCT/US2009/039759 filed Apr. 7, 2009, which is incorporated by reference herein in its entirety.

FIELD OF THE INVENTION

The present invention relates to the field of ostomy pouches, in particular, drainable ostomy pouches.

BACKGROUND TO THE INVENTION

A number of patents and published applications teach a drainable ostomy pouch, the walls of which define a narrowed drain chute for draining the pouch contents. The pouch includes an integrated closure system for sealing the pouch closed by rolling or folding the drain chute towards the main body of the pouch. The closure system includes one or more flaps that fold partly around, under or over, the rolled-up drain chute when in its closed configuration, either as a primary or secondary arrangement for retaining the drain chute in the closed configuration. Example patents and published applications include U.S. Published Application US200510131360 and U.S. Pat. Nos. 3,825,005, 7,306,581, 6,589,221 and 6,780,172. In the last two of the listed patents, the drain may be folded-up a further time, and the tip tucked behind the skirt edge of a comfort panel to partly conceal the drain.

The provision of one or more flaps may, in some situations, be undesirable. The flaps generally add to complexity of manufacture. Fasteners need to be provided for fastening the flaps in their folded condition. As well as cost, the flaps and the flap fasteners may add undesirably to the material thickness and rigidity when the drain chute is in its closed configuration. A further potential disadvantage is that, while some wearers may desire a secondary retainer arrangement, such as flaps, for the drain chute, other wearers may not desire to use a secondary retainer arrangement. The use of an ostomy pouch represents a highly personal activity, and different wearers have different preferences about how a pouch should be worn and used. However, the provision of security flaps as a secondary retainer more or less obliges the wearer to deploy the secondary retainer, otherwise the unsecured flaps may be uncomfortable for the wearer, and the exposed flap fasteners could catch on the wearer's clothing or undergarments. In order to satisfy all wearers' preferences, different designs of pouch have to be manufactured, those with the security flaps for a secondary retainer arrangement, and those without any secondary retainer arrangement. This increases inventory and manufacturing costs.

U.S. Pat. Nos. 6,726,667 and 6,887,222 teach similar drainable ostomy pouches without any flap, by using only fasteners provided directly on the face of the pouch wall to hold the drain in its closed configuration. However, such designs of pouches do not provide any integral facility for a secondary retainer should a user desire. Moreover, such pouches highlight a different potential vulnerability, namely that the rolled-up drain is substantially exposed, and is vulnerable to accidental release should an exposed edge of the drain be caught by, for example, the user's clothing or undergarments. Also, a pouch with an exposed drain when in the closed condition may be perceived by some users to be less reliable than a pouch in which the drain is somehow concealed or covered.

The present invention has been devised bearing these issues in mind.

SUMMARY OF THE INVENTION

The invention provides a pocket associated with a wall of the pouch, for receiving at least a portion of a drain chute when in its closed configuration.

In one form, the pouch drain is free of flaps with fasteners (in other words, no flaps with fasteners are present for securing the flaps in a closed configuration). In one form, the pouch drain is entirely free of flaps.

In one form, the pocket is configured with a sling portion that, in use, obstructs the drain from extending to its open configuration while received at least partly in the pocket. The pocket thereby provides a security feature for retaining the drain in its closed configuration without the need for a security flap.

In one form, the pocket is evertable as the drain is inserted into and/or withdrawn from, the pocket.

In one form, the pocket includes a mouth. The pocket is configured so that the mouth faces a direction different from that in which the drain extends when in its open configuration. For example, the pocket mouth may face generally towards a stomal aperture of the pouch, whereas the drain may extend away from the stomal aperture when in its open configuration. Also, the pocket mouth may face generally upwardly (when the pouch is viewed in a normal upright orientation in which the pouch is worn), whereas the drain may extend downwardly when in its open condition. The portion of the drain that is inserted into the pocket may be received through the mouth.

Additional aspects, features and advantages of the invention will become apparent from the following description of preferred embodiments. Protection may be sought for any novel feature or idea disclosed herein and/or illustrated in the drawings whether or not emphasis has been placed thereon.

BRIEF DESCRIPTION OF THE DRAWINGS

FIG. 16 is a schematic partial sectional view showing a modified drain chute portion in an open position.

FIG. 17a is a schematic partial sectional view similar to FIG. 16, but showing the drain chute portion with an initial fold towards a closed position with the roll started below the reinforcing member.

FIG. 17b is a schematic partial sectional view similar to FIG. 16, but showing the drain chute portion with an initial fold towards a closed position with the roll started above the reinforcing member.

FIG. 17c is a schematic sectional view showing the roll of FIG. 17b after it has been rolled above the reinforcing member.

FIG. 17d is a schematic side sectional view showing the folding of the drain chute portion of the pouch of FIG. 17a.

DETAILED DESCRIPTION OF PREFERRED EMBODIMENTS

Figure 1:
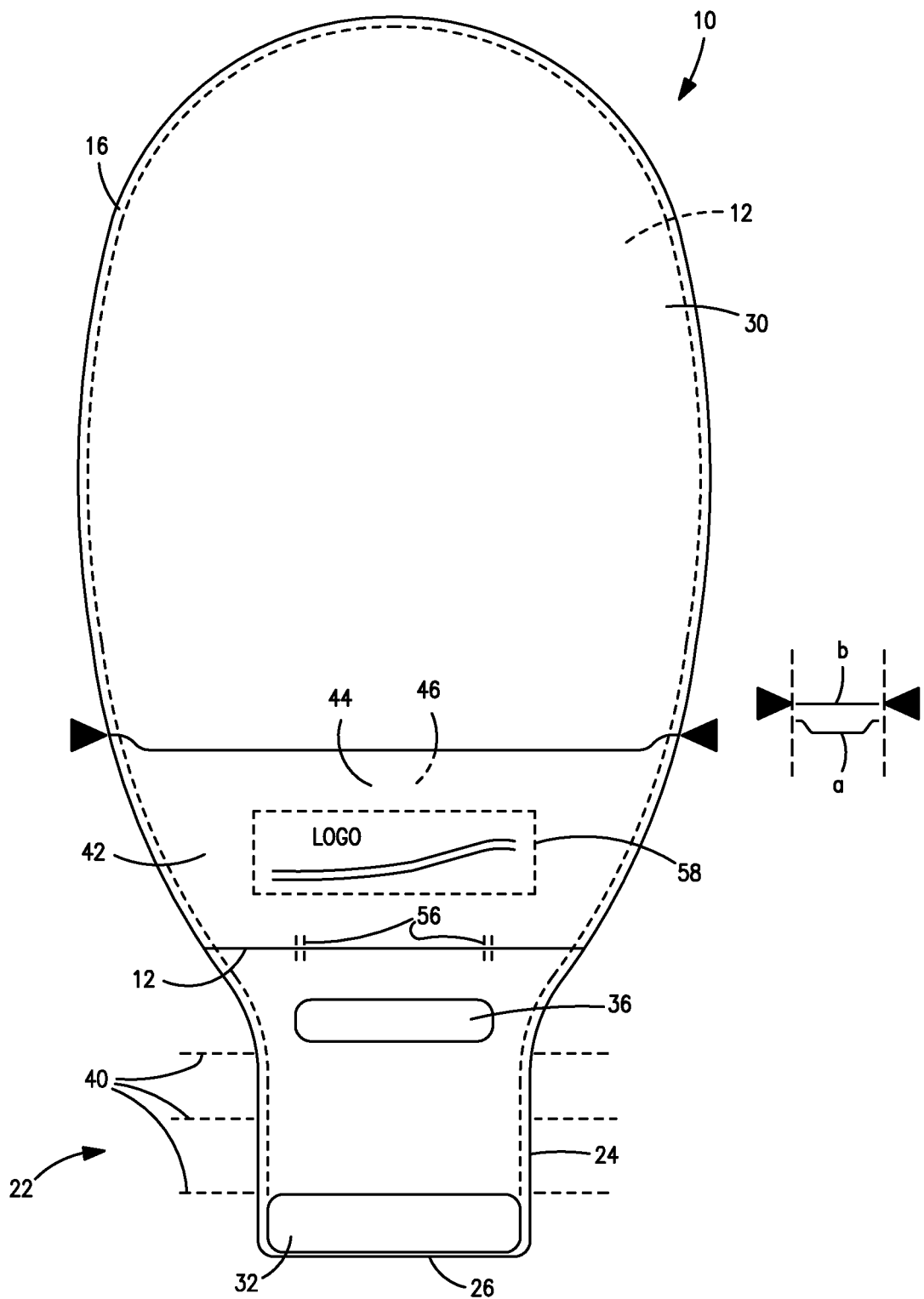
FIG. 1 is a schematic front view of a first embodiment of ostomy pouch in its open configuration.

Preferred embodiments of the invention are now described with reference to the accompanying drawings. The drawings depict ostomy pouches in a generally upright orientation in which the pouches are normally worn. The same reference numerals depict equivalent features in each embodiment.

FIGS. 1 to 8 illustrate a first embodiment of ostomy pouch 10 comprising a front wall 12 and a rear wall 14 of flexible impermeable plastics film, welded together around a common peripheral seam 16. Many suitable materials for the walls 12, 14 are known in the art. For example, the material may be a laminate of one or more layers of ethylene vinyl acetate (EVA) and a barrier layer, for example, of poly vinylidene chloride (PVDC).

The rear wall 14 of the pouch 10 has an entrance aperture 18 in its upper region for receiving human waste from a wearer's stoma. In the illustrated embodiment, the pouch 10 is intended as an ileostomy pouch for receiving semi-solid ileal fluid from a wearer's ileal stoma. The pouch 10 is securable to the peristomal area of the wearer's body by a body fitment, indicated generally at 20. The body fitment 20 typically includes a pad or wafer of hypoallergenic skin adhesive (not shown). The pouch may be of a so-called "one piece" type in which the body fitment 20 is permanently secured to the rear wall 14 of the pouch 10 at or around the entrance aperture 18. Alternatively, the pouch 10 may be of a so-called "two-piece" type in which the pouch 10 and the body fitment 20 are separate items, and are removably attachable to each other by an ostomy coupling. An example coupling includes an adhesive ostomy coupling or a mechanical ostomy coupling.

As is conventional, the pouch 10 may include one or more internal compartments (not shown) for accommodating the human waste collected in the pouch 10. Additionally or alternatively, the pouch 10 may include a known deodorizing filter (not shown) for venting and deodorizing flatus from the interior of the pouch 10. The deodorizing filter may be mounted to communicate with a vent aperture, for example, in one of the front and rear walls 12, 14.

The pouch 10 includes an outlet 22 in the form of a drain chute portion 24 of the pouch 10. The drain chute portion 24 is narrower than the upper portion of the pouch 10. As can be seen in the drawings, the drain chute portion 24 may be disposed generally symmetrically with respect to the entrance aperture 18. However, alternatively (not shown), the drain chute portion 24 may be generally asymmetrical with respect to the entrance aperture 18.

The drain chute portion 24 is defined by extensions of the front and rear walls 12, 14 that are welded together at the sides of the drain chute portion 24. A discharge opening 26 is defined between unsecured distal edges of the front and rear walls 12, 14. In the illustrated embodiment, the front and rear walls 12, 14 are generally coterminous. However, in an alternative embodiment (not shown), one of the front and rear walls 12, 14 may project beyond the peripheral edge of the other, such that the discharge opening is defined by, or between, stepped walls. Alternatively, the discharge opening 26 may instead be provided as a slit in one of the walls 12, 14.

An exterior face of one or both of the front and rear walls 12, 14 may be at least partly covered by a comfort layer 30. The comfort layer 30 may be an additional panel outside the front wall 12 and/or rear wall 14, and secured to the pouch at, for example the peripheral seam 16. Alternatively, the comfort layer 30 may be a surface layer carried by, or forming part of, the respective wall 12, 14. The comfort layer 30 is typically made of a soft cushioning material. A typical material includes a woven, nonwoven, or an apertured plastics film. The comfort layer 30 may be elastically stretchable, or it may be substantially non-stretchable. The comfort layer 30 may end at a location just above the drain chute portion 24 so as to avoid the comfort layer 30 from interfering with fasteners 34 for closing the outlet 22, as described below. It may also be desirable not to provide the comfort layer 30 in the region of the discharge opening 26, as the comfort layer 30 may be of a material that soils easily, or is difficult to wipe clean. However, alternatively, the comfort layer 30 may extend at least partly down the exterior of the drain chute portion 24, if desired.

There now follows a description of a closure system, integral with the pouch 10, for sealing the drain chute portion 24 closed. While this closure system is highly preferred, other types of integral and non-integral closure systems may be used as desired. An integral closure system is preferred as this can provide a compact size, beneficial to the pockets used in this invention (as described later). The illustrated embodiment is similar to the arrangement described in the aforementioned U.S. Pat. No. 7,306,581 to which reference may be made for further details. The closure system comprises one or both of:

(a) At least one resiliently flexible reinforcing member 32 attached to at least one of the front and rear walls 12, 14 at the drain chute portion 24. In the illustrated form, the reinforcing member 32 is positioned at, or near, the discharge opening 26. In an alternative form described later with respect to FIGS. 16, 17a, 17b, 17c and 17d, the reinforcing member 32 is spaced from the discharge opening 26. The (or each) reinforcing member 32 may be attached along its length to the wall 12, 14. In the illustrated form, the reinforcing member 32 is attached to the exterior face of the wall 12, 14, but the reinforcing member 32 could instead be attached to the interior face, or embedded in the wall 12, 14. Purposes and advantages of the reinforcing member(s) 32 may include one or more of the following:

(i) to define a unit fold-interval by which the drain chute portion 24 is folded-up into its closed configuration (as described later);

(ii) to enable the degree of distension of the discharge opening 26 to be controlled. For example, the reinforcing member 32 may bias the discharge opening 26 naturally towards an at least partly closed, or constricted condition. The reinforcing member 32 may have a generally planar shape that biases the discharge opening 26 closed, or it may have a curved or bowed natural shape to bias the discharge opening 26 slightly, or fully open, depending on the degree of bowing. The reinforcing member 32 may be manipulated manually, either by squeezing the reinforcing member 32 at its opposite edges to bow the reinforcing member 32, or by pressing the face of the reinforcing member 32 to flatten it. Typically, the reinforcing member 32 is made of a resiliently flexible plastics material that is not compressible. However, a compressible material, such as a compressible foam, may be used if desired; and or (iii) to provide a seal when the outlet 22 is rolled or folded-up. It is preferred that the reinforcing member 32 extend entirely across the width of the internal passage within the drain chute portion 24, to at least partly overlap the peripheral weld seam 16. If multiple reinforcing members 32 are used, then either at least one reinforcing member 32 extends entirely across the width of the internal passage, or the combined footprint of the reinforcing members 32 extends across the width of the internal passage.

In the illustrated embodiment, two reinforcing members 32 are provided; one attached to each wall 12, 14. The reinforcing members 32 preferably at least partly overlap each other, although the reinforcing members 32 may be partly or wholly offset with respect to each other in an axial and/or transverse direction of the drain chute portion 24 as desired. The reinforcing members 32 are spaced from each other by the film material of one or both walls 12, 14, such that the reinforcing members 32 do not directly contact each other. However, if desired, the reinforcing members 32 may contact each other at one or more points, either permanently, or when the drain chute portion 24 is placed in its closed configuration.

Figure 6:
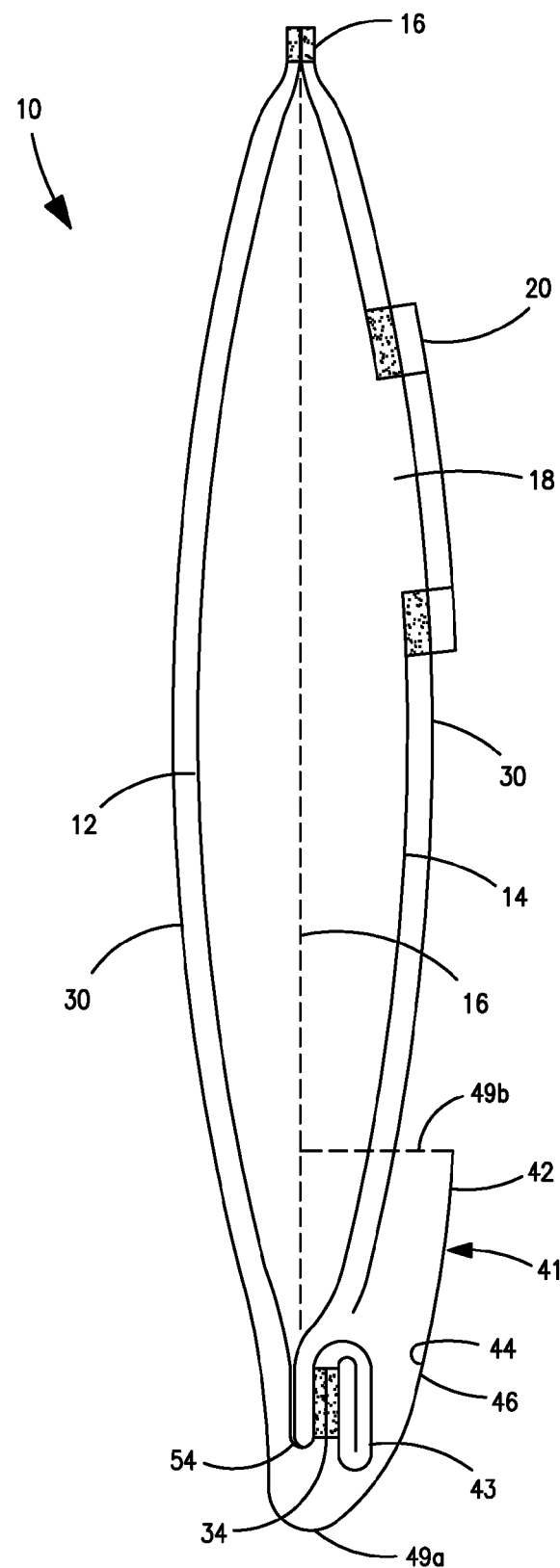
FIG. 6 is a schematic side sectional view through the pouch showing the drain chute portion received in the pocket.

(b) A fastener 34 for fastening the drain chute portion 24 in a rolled-up closed configuration, as illustrated in FIG. 6. The fastener 34 generally comprises first and second fastener parts 36, 38 on the front and rear walls 12, 14, respectively. Each fastener part 36, 38 may be an element that is attached to the wall 12, 14, or it may comprise a surface of the respective wall 12, 14 itself. In the preferred form, the fastener part 36, 38 is a peelable, distributed mechanical engagement fastener, such as a hook-loop type, or an interlocking male-male type, e.g., interlocking mushroom heads, or interlocking hooks. In an alternative form, the fastener 34 may be of a peelable-resealable adhesive type, including at least one adhesive surface for adhesively engaging either a complementary adhesive, or non-adhesive, landing surface, such as a wall of the drain chute portion 24. The fastener 34 may be one part. The fastener parts 36, 38 may be the same as each other (in terms of material and/or configuration), or the fastener parts 36, 38 may be different. The fastener parts 36, 38 may be of the same size as each other. Alternatively, one fastener part (e.g., 36) may be larger than the other (e.g., 38), at least in a dimension in corresponding to the direction of folding (e.g., the up-down direction when the ostomy pouch 10 is viewed in the upright orientation). Such dimensioning can provide full supportive contact with the smaller part, notwithstanding different manufacturing and folding tolerances that may affect the exact positional relation between the fastener parts 36, 38 when the drain chute portion 24 is moved to its closed condition. Such a feature may be advantageous to ensure that the drain chute coil 43 is fully secured and supported, even if the wearer decides not to deploy secondary retention.

In the illustrated embodiment, the reinforcing members 32 and the fastener parts 36, 38 are distinct items from one another. However, at least one of the fastener parts 36, 38 may be integrated with a respective reinforcing member 32, if desired.

Figure 2:
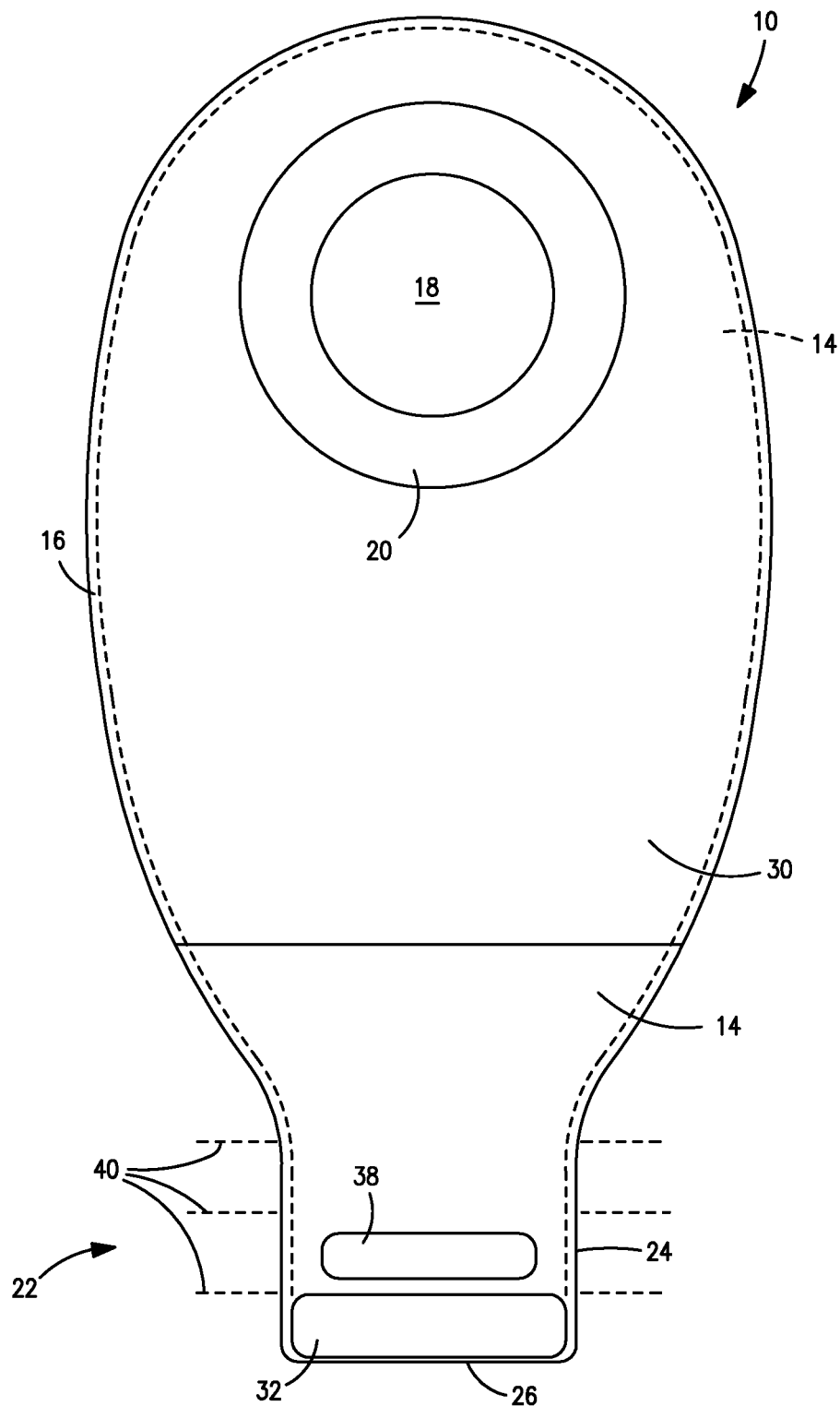
FIG. 2 is a schematic rear view of the pouch of FIG. 1.
Figure 3:
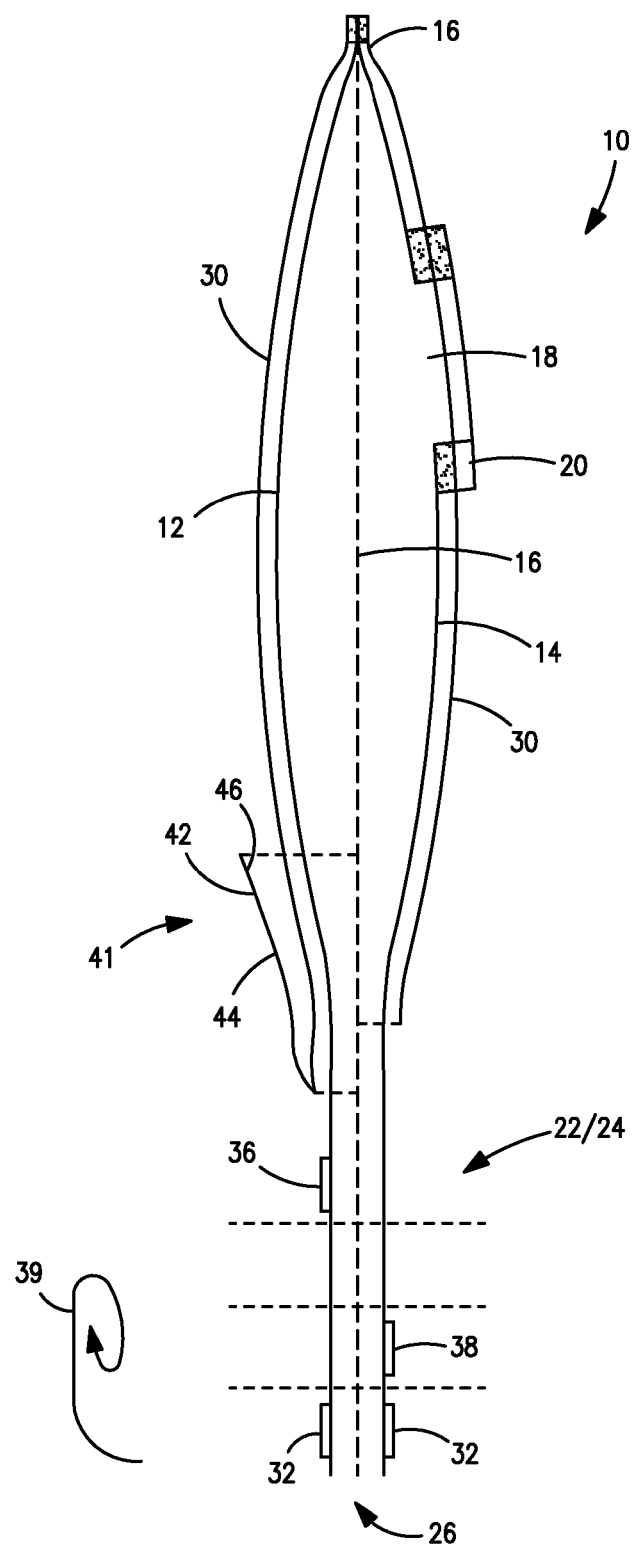
FIG. 3 is a schematic side sectional view through the pouch of FIG. 1.
Figure 4:
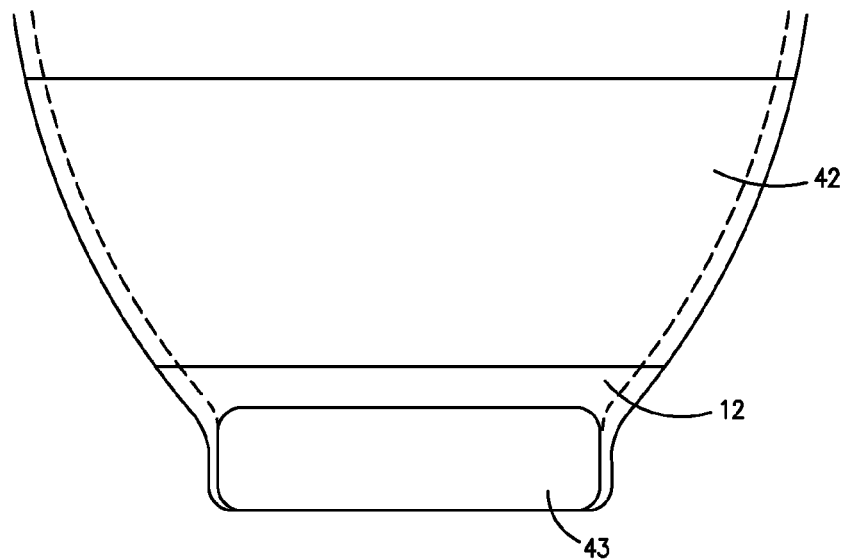
FIG. 4 is a schematic front partial view of the pouch of the first embodiment, with the drain chute portion folded to a closed condition prior to insertion in the pocket.

FIGS. 1 to 3 show the drain chute portion 24 in its open configuration for permitting discharge of stomal effluent from the pouch 10. In order to close the drain chute portion 24, the drain chute portion 24 is folded (indicated by arrow 39 in FIG. 3) one or more times around notional fold lines 40 (such as defined by the unit size of the reinforcing members 32). As shown in FIG. 4, the drain chute portion 24 is folded upwardly three times to its closed configuration, but a greater or smaller number of folds may be implemented as desired. The folding brings the drain chute portion 24 to its closed configuration in which, in this embodiment, a coil 43 is formed. The fastener parts 36, 38 are so positioned that folding of the drain chute portion 24 to its closed position brings the fastener parts 36, 38 into register with each other. The fastener parts 36, 38 are mutually engaged by a finger-pressure squeezing of two fastener parts 36, 38, thereby securing the drain chute portion 24 in its closed position.

As mentioned above, other types of integral or non-integral closure systems may be implemented as desired. For example, either the reinforcing members 32 or the fastener 34 or the fastener parts 36, 38 may be omitted, or an entirely different closure system may be used.

A feature of the preferred embodiments is a pocket 41 for at least partly receiving the drain chute portion 24 when in its closed configuration. In the present embodiment, the pocket 41 is defined on an external portion of the pouch 10 by an evertable pocket wall 42 that forms a cuff with respect to a face of the pouch 10, for example, the face of the front wall 12 when in an initial state. The evertable pocket wall 42 is attached to the peripheral weld 16 of the pouch 10. The evertable pocket wall 42 includes a first face 44 that initially faces outwardly away from the pouch 10, and a second face 46 that initially faces inwardly towards the pouch 10.

Figure 5:
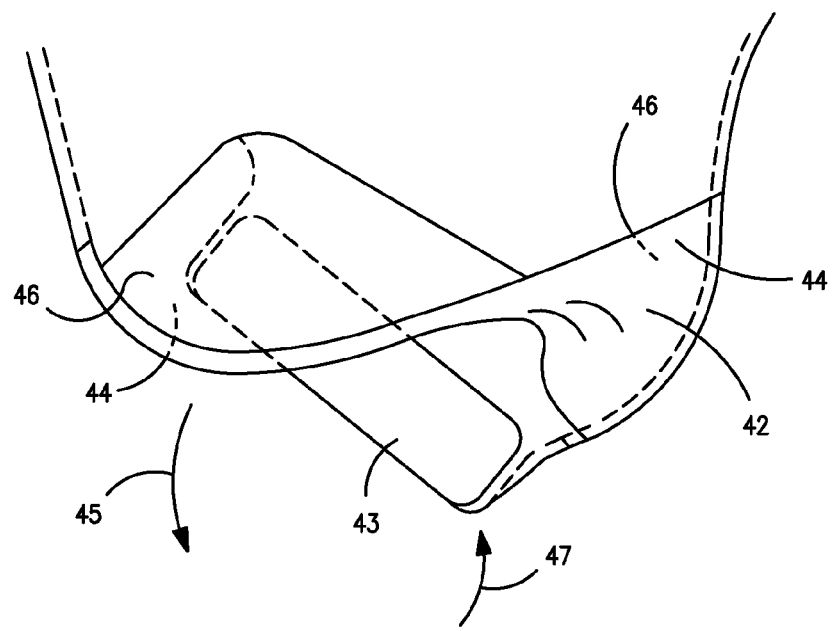
FIG. 5 is a schematic front partial view of the pouch of the first embodiment, showing an initial stage of insertion of the drain chute portion into the pocket.
Figure 7:
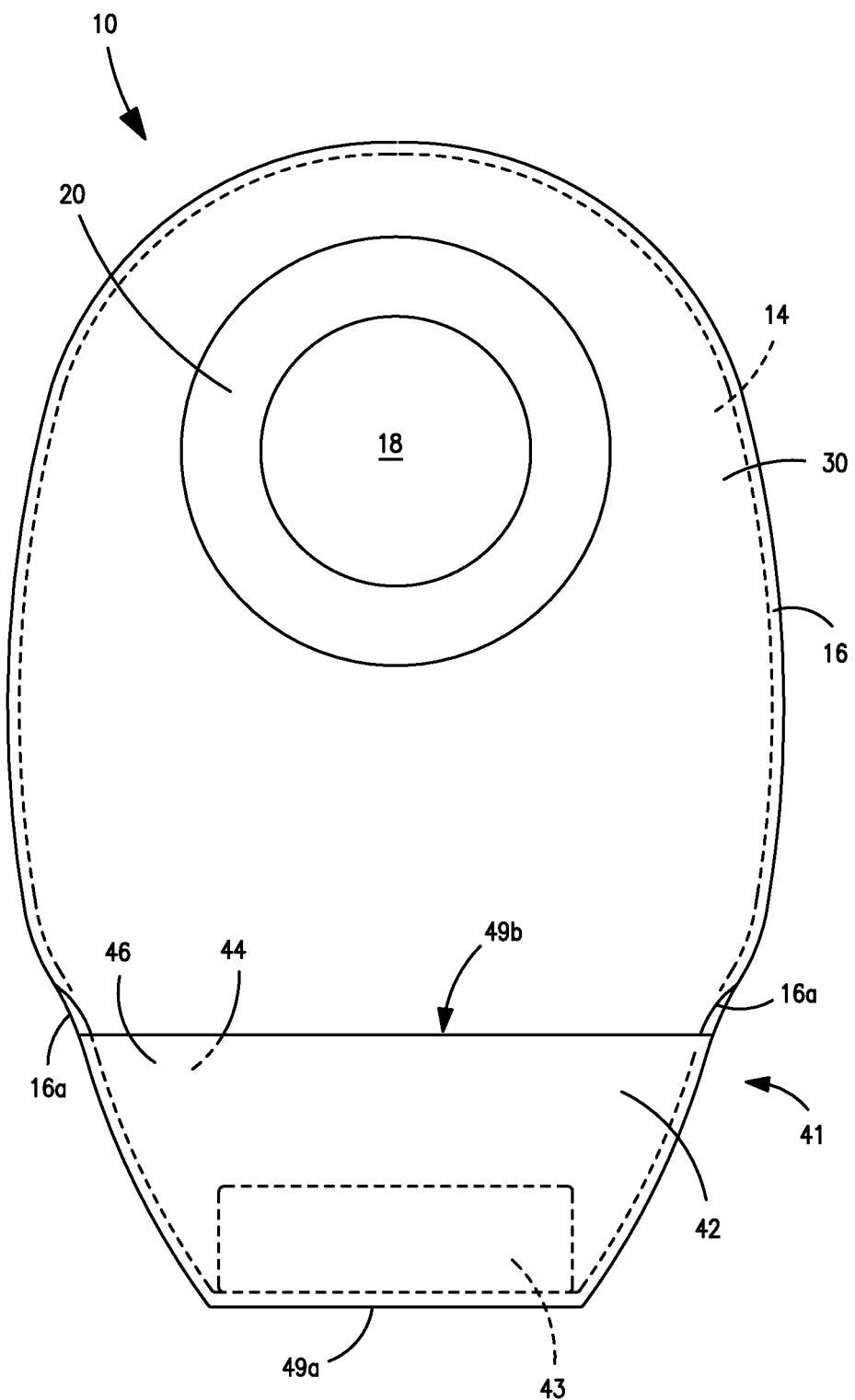
FIG. 7 is a schematic rear view of the pouch in the configuration of FIG. 6.

Referring to FIG. 5, in order to insert the drain chute portion 24 into the pocket 41, the evertable pocket wall 42 is everted over the folded-up drain chute portion 24. This is easily performed by drawing the evertable pocket wall 42 (e.g., downwardly, as indicated by arrow 45) over the exposed drain chute portion 24, while the drain chute portion 24 is pressed gently in the opposite direction (e.g., upwardly, as indicated by arrow 47). This action everts the wall 42 over to the opposite face of the pouch (e.g., to the face of the rear wall 14), as shown in FIGS. 6 and 7, and such that the pocket wall 42 cups around and contains the drain chute portion 24. It will be appreciated that the pocket 41 is technically present in the initial state shown in FIGS. 1-4, but is less apparent, because the pocket 41 is turned inside out when in the initial state. Everting the pocket wall 42 over the rolled-up drain chute portion 24 manifests the pocket 41. The first face 44 now faces inwardly towards the pouch 10 and defines an interior face of the pocket 41, and the second face 46 now faces outwardly away from the pouch 10, and defines an exterior face of the pocket 41.

In the present arrangement, the action of everting the pocket wall 42 adds a turn or fold 54 to the material of the drain chute coil 43, as can be seen in FIG. 6, and as can also be appreciated by comparing FIGS. 5 and 7. The addition of an extra fold 54 increases the security of the closure system, by increasing the number of folds that the effluent would have to pass before reaching the discharge opening 26. This additional fold 54 is gained without the wearer having to fold the coil 43 further manually, potentially enabling a reduction in the number of folds that a wearer is required manually to include in the coil 43. The added fold 54 may be in same direction as the other folds in the coil 43, or the opposite direction, depending on whether the coil 43 is normally folded up on the opposite side or same side, respectively, as the evertable pocket wall 42 when in its initial position. In the present embodiment, the coil 43 is folded-up on the same side as the evertable pocket wall 42 when the evertable pocket wall 42 is in its initial position. The additional fold 54 is in the opposite direction to the folds in the coil 43. Providing the additional fold 54 in the opposite direction may enable a tighter fold 54 than if the fold 54 is in the same direction around the bulk of the already-formed coil 43. A tighter fold 54 enhances security against leakage of effluent past the fold 54. However, the relative direction of the added fold 54 may be configured as desired.

The evertable pocket wall 42 may be made of the same material as the comfort layer 30, or the evertable pocket wall 42 may carry a comfort layer 30 on the first and/or second faces 44, 46. A preferred construction of the pocket 41 is described later below with respect to FIG. 8.

As can be seen in FIG. 6, a lower portion 49a of the pocket 41 extends as a sling that supports the drain chute portion 24 in its closed configuration, and obstructs the drain chute portion 24 from extending to its open configuration. The pocket 41 thereby provides a security feature for retaining the drain chute portion 24 in its closed configuration without the need for a security flap, and without the need to provide a dedicated fastener for holding the pocket 41 over the drain chute portion 24. The avoidance of such a flap and associated fastener provides significant cost and manufacturing advantages. A mouth 49b of the pocket 41 faces in a direction that is generally opposite to the direction in which the drain chute portion 24 extends when open. The evertable wall 42 and the confronting face of the pouch 10 define a permanently formed sleeve portion of the pocket 41 communicating with the mouth 49b, and in which the drain chute portion 24 is at least partly received. The pocket 41 is permanently attached to, or an integral part of, the pouch 10.

The pocket 41 also serves to hold the drain chute portion 42 in its folded configuration, with a retention force that increases as the ostomy pouch 10 becomes increasingly full of effluent. As the ostomy pouch 10 becomes full, and swells outwardly, this increases the force pressing the coil 43 against the everted pocket wall 42 covering the coil 43, thereby (i) further compressing the folds and reducing the risk of leakage, and (ii) increasing the retention of the coil 43 by the pocket wall 42. In other words, the weight of the effluent in the ostomy pouch 10 is used to generate a sealing pressure pressing the coil 43 into even tighter engagement by the everted pocket wall 42. This is a significant advantage achievable by a pocket 41, compared to a more conventional ostomy pouch in which there is no facility to use the weight of the effluent to generate a sealing force, or in which the sealing force is reduced as a result of fastener play. In such conventional pouches, the seal strength at the outlet may decrease as the pouch becomes fuller.

It will be appreciated that, since the evertable pocket wall 42 is formed attached to the ostomy pouch 10 in its initial position (FIGS. 1 and 3), and is everted to the opposite face of the ostomy pouch 10 (FIGS. 6 and 7), the evertable pocket wall 42 has to extend around the peripheral seams 16 on either side, as well as overlap the opposite face of the ostomy pouch 10. There may be a tendency for the evertable pocket wall 42 to slightly constrict the lower portion of the ostomy pouch 10 when in its everted position. Such constriction may be avoided or reduced by either, or both, of:

(i) Making the evertable pocket wall 42 of resiliently stretchable material. For example, the pocket wall 42 may have a Young's modulus of less than 0.1 GPa. Such a stretchable material may enable the evertable pocket wall 42 to lie substantially flat against the ostomy pouch face under most situations without unduly constricting the ostomy pouch 10; for example, in the initial position (FIG. 3), and in the everted position (FIG. 6), whether the ostomy pouch 10 is empty and flat, or is full and bloated in shape.

(ii) Dimensioning the evertable pocket wall 42 to be slightly larger (in at least one dimension, such as laterally), than the portion of the ostomy pouch wall 12, 14 that the evertable pocket wall 42 overlies when the evertable pocket wall 42 is in its initial position. For example, referring to FIG. 1, the largest width of the evertable pocket wall 42 (dimension "a" as measured adjacent to the mouth) may be slightly greater than the width "b" of the ostomy pouch 10 at the same position. The difference between "a" and "b" may be less than 1 cm, preferably less than 0.7 cm, more preferably less than about 0.6 or 0.5 cm. The difference may be approximately equal to or between about 1 and about 2 times the width of the seam 16 (at that point). The difference in lateral dimension may cause the evertable pocket wall 42 to hang slightly away from the ostomy pouch face when the evertable pocket wall 42 is in its initial position (as depicted in FIG. 3). In use, when the evertable pocket wall 42 is everted to form the pocket 41, the longer dimension "a" accommodates the seam 16 of the ostomy pouch 10, and enables the evertable pocket wall 42 to lie flat against the rear face 14 without unduly constricting the ostomy pouch 10 even when full.

When in the pocket 41, the drain chute portion 24 (coil 43) is substantially concealed and protected against the drain chute portion 24 accidentally catching on the wearer's undergarment or clothing. The evertable pocket wall 42 also aids comfort and discretion by covering any abrupt edges of the rolled-up drain chute portion 24. The evertable pocket wall 42 can have a very low profile and lie closely adjacent the face of the pouch 10, leading to a very discrete pouch 10. In the configuration of FIGS. 6 and 7, the only visual sign may be a slight folding of the seam 16 at points 16a, as the seam 16 is inverted in the pocket 41.

Also, the user is not obliged to use the pocket 41 if the user prefers not to. Should the user prefer not to use the evertable pocket wall 42 to create the pocket 41, the evertable pocket wall 42 remains neatly and discretely on the face of the pouch 10 in its initial state, and does not flap loosely or untidily as would an unsecured flap. The provision of the evertable pocket wall 42 does not complicate significantly the manufacturing process, nor does it add significantly to material cost. Thus, the same design of pouch 10 can be provided as a universal pouch suitable for both: (i) users who desire to use a secondary security feature for retaining the drain chute portion 24 in its closed configuration; and (ii) users who do not desire to use such a secondary security feature. In such a case, it may be desirable that the evertable pocket wall 42 be made of, or present on both faces 44, 46, comfort layer material.

The manipulation required to open the drain chute portion 24 is a straightforward reversal of the process described above, namely (i) un-everting the pocket wall 42 to thereby withdraw the pocket 41 from around the folded drain chute portion coil 43 (as in FIG. 4); (ii) peeling the fastener parts 36, 38 apart to release the drain chute portion 24; and (iii) unfolding the drain chute portion 24 to its fully extended condition (as in FIGS. 1-3).

In the present embodiment, the pocket 41 is provided as a secondary retainer for retaining the drain chute portion 24 in its closed configuration, and the fastener 34 provides a primary retainer function. However, if desired, the fastener 34 may be omitted, and the pocket 41 may be configured to provide a primary retainer function. This can enable the drain chute portion 24 to be retained closed without a fastener. It will be appreciated that the arrangement of the evertable pocket wall 42 can provide as tight a retention function as may be desired, because the pocket 41 is created automatically over the drain chute portion 24 as the pocket wall 42 is everted.

Figure 8:
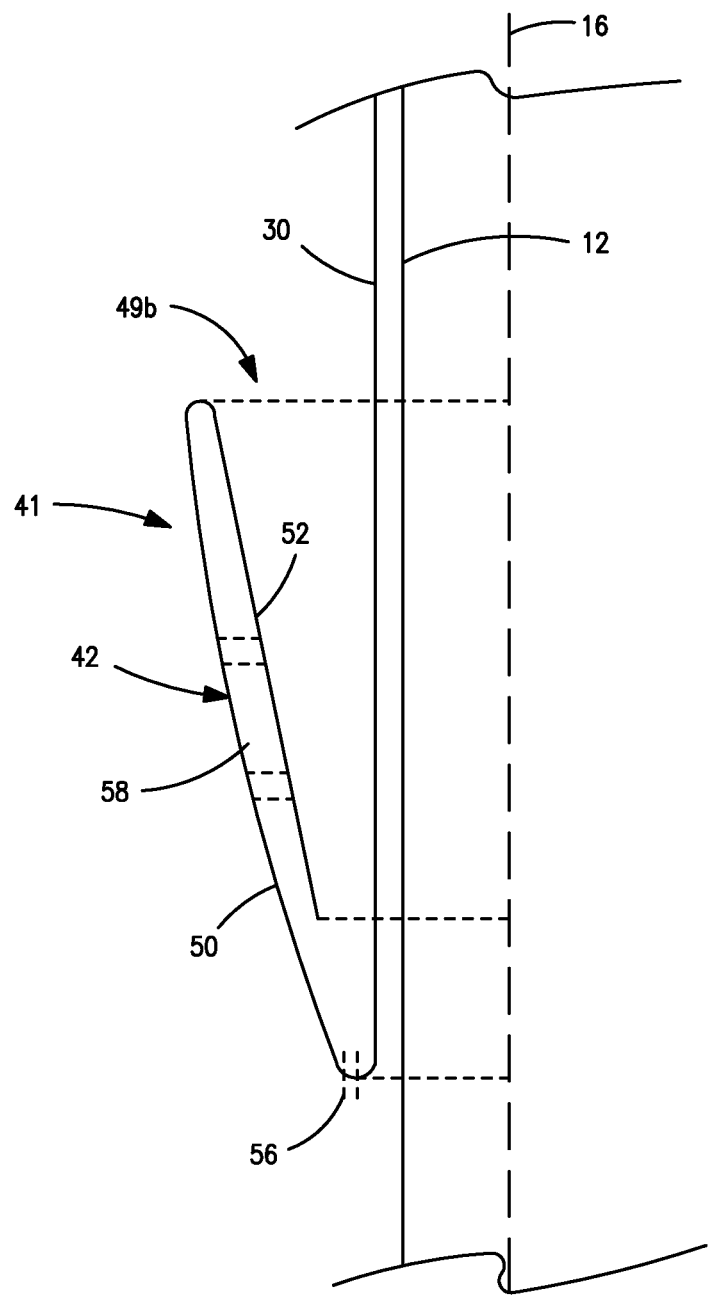
FIG. 8 is a schematic sectional view showing on an enlarged scale the construction detail of the pocket of the first embodiment.
Figure 9:
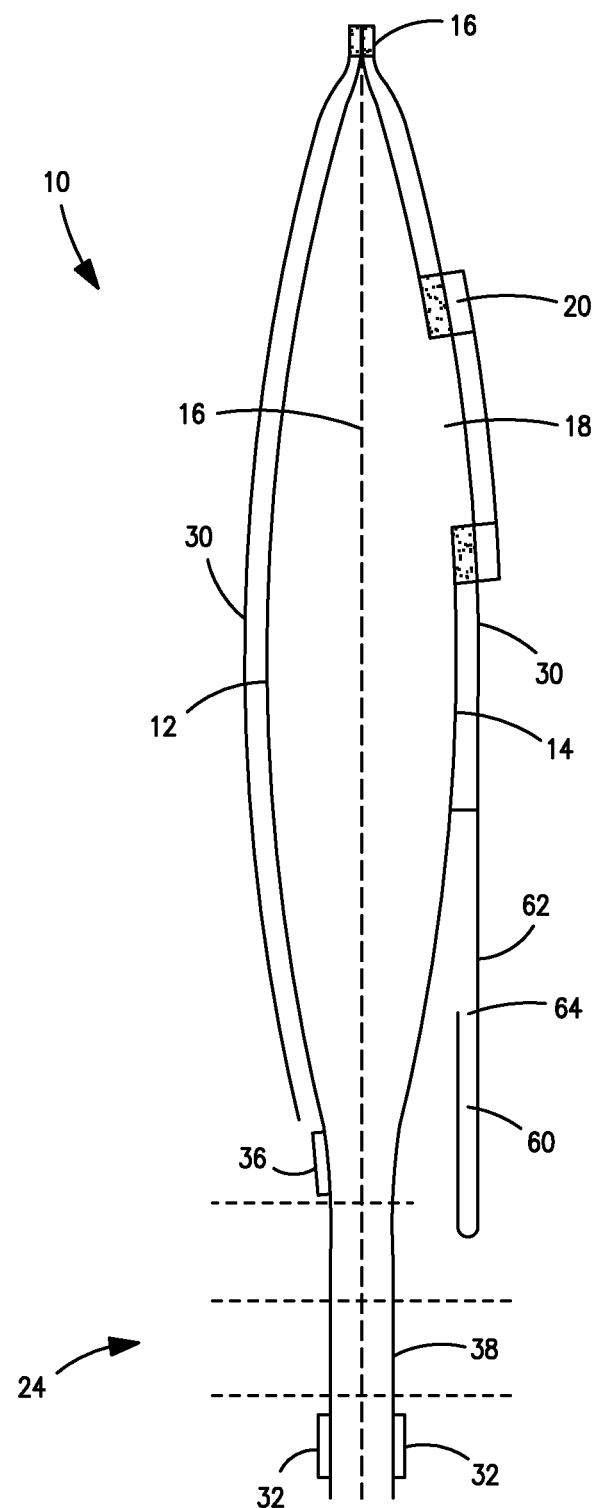
FIG. 9 is a schematic side sectional view through a second embodiment of ostomy pouch in its open configuration.
Figure 10:
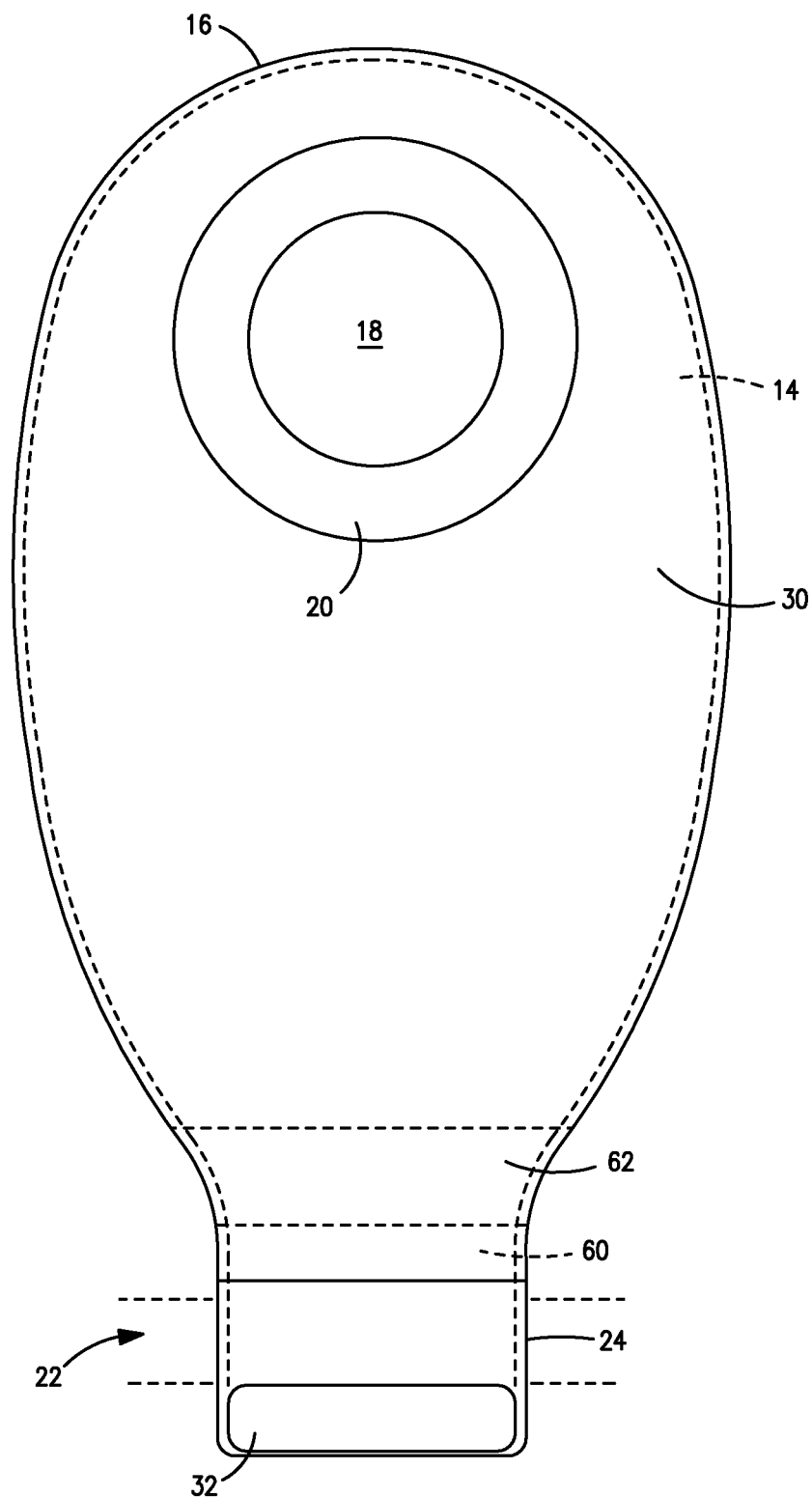
FIG. 10 is a schematic rear view of the arrangement in FIG. 9.

The evertable pocket wall 42 may be made of any suitable material as desired, including plastics film, a combination of plastics film and a comfort layer 30, or merely of comfort layer material. Referring to FIG. 8, a preferred construction of the evertable pocket wall 42 is as an extension of the comfort layer 30. The evertable pocket wall 42 is formed by a first extension 50 that is folded upwardly with respect to the comfort layer 30, and a second extension 52 of the first extension 50. The two extensions 50, 52 provide dual plies of material to provide the evertable pocket wall 42 with good strength, despite being made of comfort layer material. The side edges of the extensions 50, 52 are welded to the peripheral seam 16 of the pouch 10. The comfort layer material may be non-stretchable or it may be resiliently stretchable, to provide the optional elastic properties explained above.

The evertable pocket wall 42 may include a stiffened portion 58 for encouraging the evertable pocket wall 42 to lie flat in a planar shape. The stiffened portion 58 preferably extends at least partly in a lateral direction. The stiffened portion 58 could be provided by an additional stiffener. However, in a preferred form, the stiffened portion 58 is provided by one or more welds. The welds have the effect of making the material more rigid. The welds may secure plural plies together if the evertable pocket wall 42 is made of plural plies. The welds may be linear, and/or define a logo and/or one or more alphanumeric characters.

A further feature of the pocket 41 is that the pocket 41 is self draining. Liquid that might enter the pocket 41 via the mouth 49b can drain out of the pocket 41 via a different route. This avoids, for example, water from pooling in the pocket 41 when the wearer is showering, or when the ostomy pouch 10 is washed. In the illustrated form in which the evertable pocket wall 42 is made of comfort layer material, such material is liquid permeable, allowing liquid to drain away. If the pocket 41 is bounded by liquid impermeable material, then it is preferred to include a drain passage for draining liquid from the pocket 41. The drain passage may be formed by an aperture through the pocket wall 42, or a gap in a peripheral weld bounding the pocket 41. (A typical position of drain passage is shown at 56 in FIG. 1.)

FIGS. 9-14 illustrate a second embodiment of ostomy pouch 10 that is similar to the first embodiment in terms of the pouch construction, the drain chute portion 24, and the closure system for the drain chute portion 24. The main difference lies in the provision of a fixed pocket 60 instead of the evertable pocket wall 42 and pocket 41 of the previous embodiment.

The fixed pocket 60 is carried by a depending extension 62 on the front and/or rear of the pouch 10. In the illustrated form, the depending extension 62 is attached to the rear wall 14, but the front wall 12 could be used, if preferred. Also, the depending extension 62 is an extension of the comfort layer 30, but the depending extension 62 could additionally or alternatively comprise plastics film, or be made of other material as desired.

The fixed pocket 60 includes a mouth 64 on the side facing inwardly towards the pouch 10 and the drain chute portion 24. The pocket walls 42 define a permanently formed sleeve portion of the pocket 60 communicating with the mouth 64. The pocket 60 is permanently attached to, or is an integral part of, the pouch 10. The mouth 64 generally faces in an opposite direction to the direction in which the drain chute portion 24 is unfolded to its open configuration. For example, the mouth 64 generally faces towards the entrance aperture 18, whereas the drain chute portion 24 is unfolded to its open configuration in a direction generally away from the entrance aperture 18. From another point of view, the mouth 64 generally faces upwardly with respect to the orientation in the drawings, whereas the drain chute portion 24 is unfolded to its open configuration in a direction generally downwardly.

Figure 11:
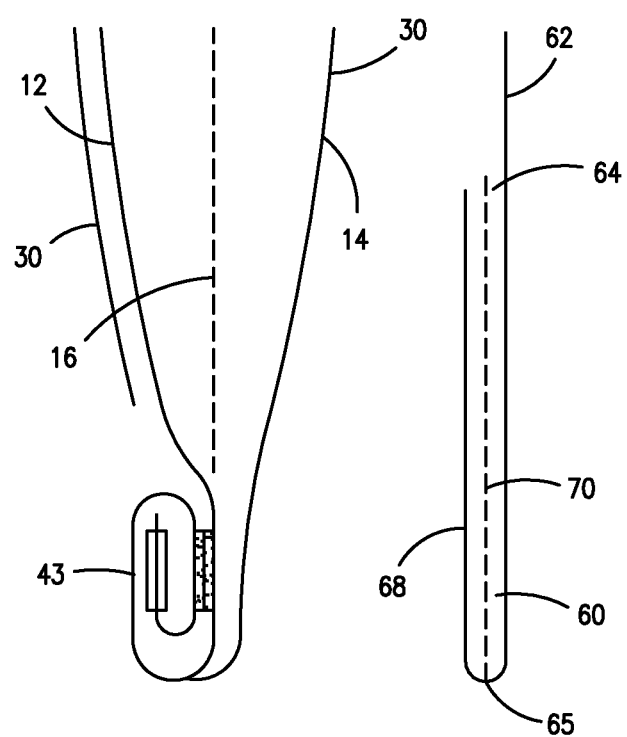
FIG. 11 is a schematic partial side sectional view showing the drain chute portion of the second embodiment in a closed configuration.
Figure 12:
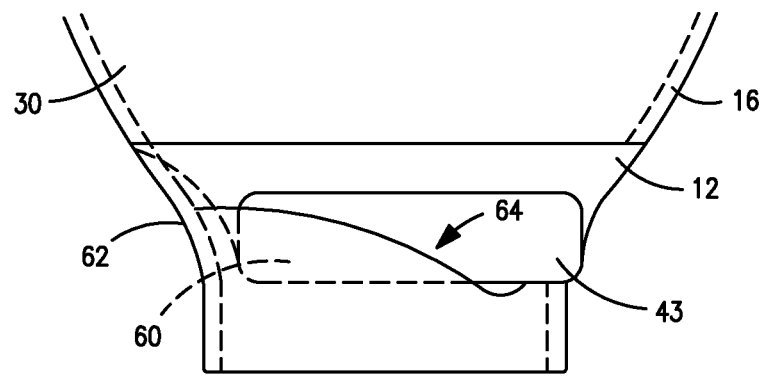
FIG. 12 is a schematic partial front view showing insertion of the drain chute portion into a pocket of the second embodiment.
Figure 13:
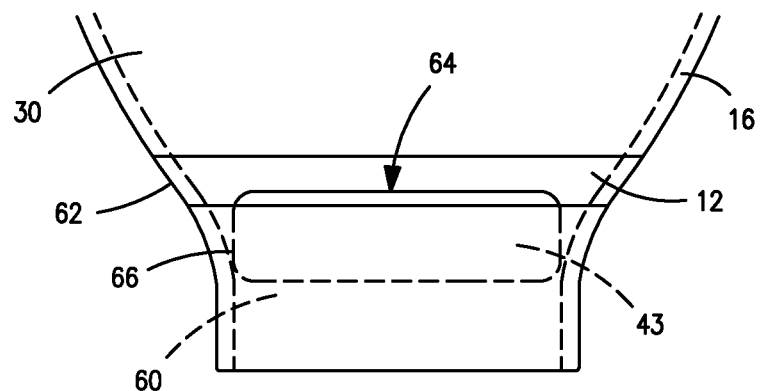
FIG. 13 is a schematic partial front view showing the drain chute portion received in the pocket of the second embodiment.

In use, the drain chute portion 24 is folded upwardly to its closed configuration, as illustrated in FIG. 11. Thereafter, the folded-up drain-chute portion coil 43 is inserted through the mouth 64 into the fixed pocket 60 (FIGS. 12 and 13). The point 63 at which the depending extension 62 meets the peripheral weld of the seam 16 can be chosen to control how the depending extension 62 hangs and moves with respect to the ostomy pouch 10 and the drain chute 24. This can be optimized to make it easy for the wearer to maneuver the drain chute coil 43 into, and out of, the fixed pocket 60.

As with the preceding embodiment, the fixed pocket 60 at least partly accommodates the drain chute portion 24. At least a portion of the fixed pocket 60 extends under the drain chute portion 24 as a sling that obstructs movement of the drain chute portion 24 to its open configuration, and thereby provides a security feature. The sling may be formed by a lower portion 65 of the fixed pocket 60 and/or by tight fitting of the side edges of the fixed pocket 60. The fixed pocket 60 substantially covers the folded-up drain chute portion 24, improving comfort against the skin, and discretion under clothing. Also, no additional fasteners are required to hold the folded-up drain chute portion 24 within the fixed pocket 60.

In the illustrated form, the fixed pocket 60 has tapered side edges 66 (FIG. 13), such that the width of the fixed pocket 60 narrows from the mouth 64 towards the bottom of the fixed pocket 60. Such a tapered configuration can increase the tightness of the fit between the fixed pocket 60 and the folded-up drain chute portion 24 the further the drain chute portion 24 is inserted into the fixed pocket 60. Alternatively, the fixed pocket 60 may have straight, generally parallel side edges 66, such that the fixed pocket 60 has a generally rectangular configuration. Preferably, the depending extension 62 and fixed pocket 60 has an outline shape that matches the profile of front panel 12 and back panel 14, and a weld which forms the fixed pocket 60 to be coterminous with the outline weld 16. Combining these welds and outline cuts simplifies the manufacturing of the ostomy pouch 10. The depth of the fixed pocket 60 can be chosen as desired. In one form, the fixed pocket 60 has a depth that substantially matches the relative position of the folded-up drain chute portion 24, so that the fixed pocket 60 complements retention of the drain chute portion 24 in that position. In another alternative, the fixed pocket 60 is deeper than relative position of the folded-up drain chute portion 24, such that the fixed pocket 60 acts as a safeguard should the drain chute portion 24 begin to drop down from its folded-up position. In yet another alternative, the fixed pocket 60 is shallower than the relative position of the folded-up drain chute portion 24, such that the fixed pocket 60 directly supports the drain chute portion 24 and can relieve forces on the fastener 34.

Figure 14:
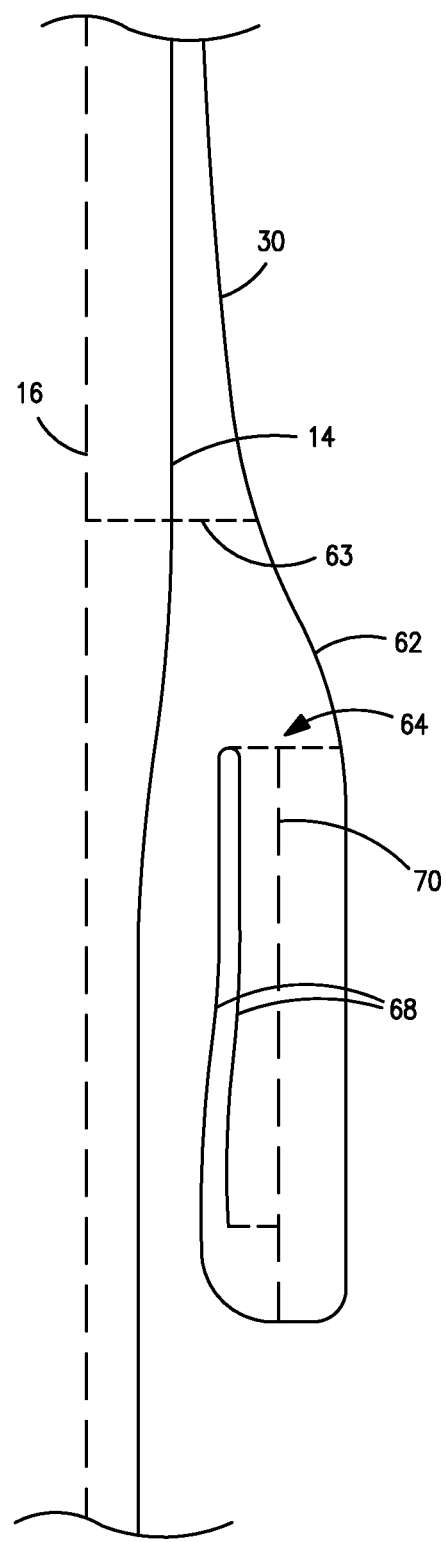
FIG. 14 is a schematic sectional view showing on an enlarged scale the construction detail of the pocket of the second embodiment.

FIG. 14 illustrates a preferred construction of the fixed pocket 60. The extension 62 provides a first pocket wall and is folded back on itself twice to provide a dual-ply opposite wall 68, in a similar manner to the first embodiment. The pocket walls are attached to each other at a pocket seam 70.

Figure 15:
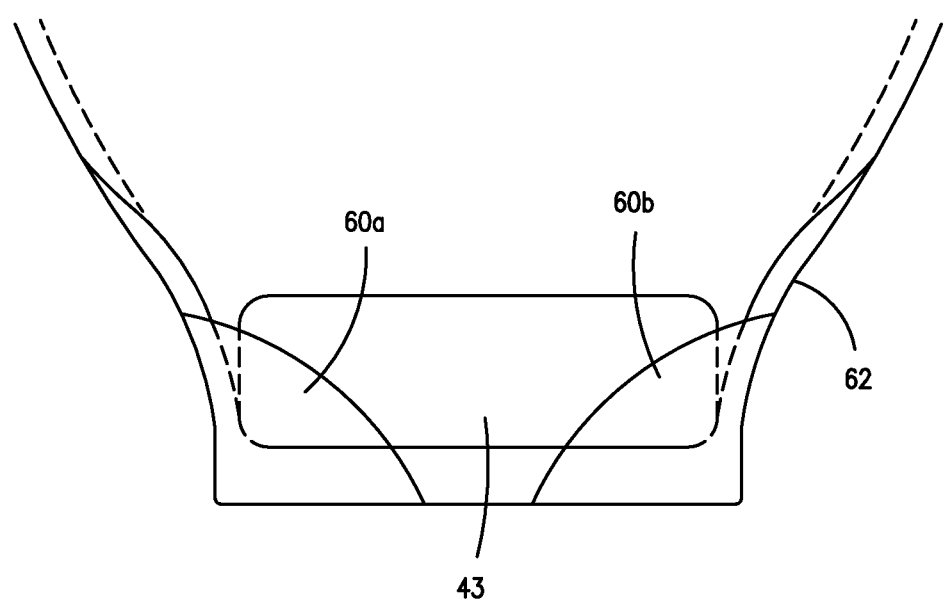
FIG. 15 is a schematic view of a modification of the second embodiment.

FIG. 15 illustrates a minor modification to the fixed pocket 60 of the second embodiment. First and second corner pockets 60a, 60b replace the full width fixed pocket 60 previously described. The corner pockets 60a, 60b are configured to receive the opposite edge portions of the folded-up drain chute portion coil 43 to retain the drain chute portion 24 captive in its closed configuration.

FIGS. 16, 17a, 17b, 17c and 17d illustrate a modification to the arrangement of reinforcing members 32 on the drain chute portion 24. This modification may be used with or without the pockets 41, 60 described above. The main difference in the modification is that at least one reinforcing member 32 is spaced from the discharge opening 26 by a distance "c" that is at least 0.5 cm, more preferably at least 1 cm, more preferably at least or about 1.5 cm. Spacing the reinforcing member 32 from the discharge opening 26 can improve hygiene for the wearer by providing a guard distance between the draining effluent, and the point at which the wearer has to handle the ostomy pouch 10 at the reinforcing member(s) 32. This can also reduce the risk of the wearer's hands being soiled by splashback from the draining effluent (which may have a highly fluid consistency). The spacing can still permit the wearer to controllably distend the drain chute portion 24 for cleaning after draining.

If an outlet fastener 34 is provided, the reinforcing member 32 is positioned between a respective outlet fastener part 36, 38, and the discharge opening 26. When rolling up the drain chute portion 24 into a closed position, the wearer can begin the first fold either below reinforcing member 32 (FIG. 17a) or above it (FIGS. 17b and 17c). In one embodiment, the distance "c" is not greater than a distance "d" between the reinforcing member 32, and the respective outlet fastener part 36 that is furthest from the discharge opening 26. Such a distance "c" ensures that a region 80 of the drain chute portion 24 between the reinforcing member 32 and the discharge opening 26 can be folded upwardly to start the folding operation, without obscuring the fastener part 36.

In a highly preferred form, the distance "c" is approximately equal to or slightly less than dimension "e" of the reinforcing member 32 that defines a unit fold length of the drain chute portion 24 (i.e., the distance between the notional fold lines 40). Such a length allows the drain chute portion 24 to be folded either below reinforcing member 32 or above it, without the material below the reinforcing members 32 interfering with the fastener 34 engagement. The importance of the drain chute portion 24 length below the reinforcing member 32 is described in FIG. 17b. The height A of the drain chute portion 24 end as rolled preferably does not exceed the height C of the bottom of fastener 36, or most preferably does not exceed height B of the top of the formed coil 43.

In an additional aspect (FIG. 17d), the invention provides a folding drain chute 82 for an ostomy pouch 10, the drain chute 82 comprising at least one reinforcing member 32 provided on a face of the drain chute 82 and spaced from a discharge opening 26 of the drain chute 82 to define a region of plastics pouch film on the face between the reinforcing member 32 and the discharge opening 26. The spacing may be at least 0.5 cm, more preferably at least 1 cm, and more preferably at least or about 1.5 cm. A footprint of the at least one reinforcing member 32 may extend substantially entirely across an internal drain passage in the drain chute 82, and preferably overlap weld seams on either side of the internal drain passage. Where the reinforcing member 32 defines a unit fold length of the drain chute 82, the spacing may optionally be approximately the same as said unit fold length. As described earlier above, the reinforcing member(s) 32 may be substantially planar to bias the drain chute 82 and/or outlet opening closed, or the reinforcing member(s) 32 may be slightly or substantially pre-bowed to bias the outlet opening and/or drain chute 82 open.

While the preferred embodiments show the ability of the invention to implement a foldable drain chute for a pouch without needing flaps with flap fasteners, such flaps with fasteners may still be used in combination with the invention if desired.

It is emphasized that the foregoing embodiments are illustrative of preferred forms of the invention. Many modifications, improvements and equivalents may be within the scope and/or spirit of the invention as claimed.

I claim:

1. A drainable ostomy pouch comprising:
    a collection portion;
    a drain chute depending from the collection portion and having a discharge opening for permitting emptying of contents from the pouch, the drain chute being foldable between an open condition in which the drain chute is extended from the collection portion, and a closed condition in which the drain chute is folded towards the collection portion;
    at least one reinforcing member permanently attached to the drain chute and associated with the discharge opening for controlling distension of the discharge opening;
    at least one fastener permanently attached to the pouch for retaining the discharge opening in the closed condition; and
    an evertable pocket for receiving at least a portion of the drain chute, the pocket including a mouth communicating with a sleeve portion, the sleeve portion being configured to obstruct the drain chute from extending to the open condition when said portion of the drain chute is received in the pocket, the pocket being configured to enable said portion of the drain chute when in the closed condition to be received in, and removed from, the pocket by everting the pocket.

2. The drainable ostomy pouch according to claim 1, wherein the pocket includes a sling portion that extends around said portion of the drain chute received in the pocket, to obstruct the drain chute from extending to the open condition.

3. The drainable ostomy pouch according to claim 1, wherein the sleeve portion is permanently formed.

4. The drainable ostomy pouch according to claim 1, wherein the pocket is permanently attached to the pouch.

5. The drainable ostomy pouch according to claim 1, wherein the pocket is disposed to enable said portion of the drain chute, when in the closed configuration, to be received in, and removed from, the pocket through the mouth of the pocket.

6. The drainable ostomy pouch according to claim 1, wherein a wall of the pocket comprises or carries a comfort layer.

7. The drainable ostomy pouch according to claim 1, wherein the sleeve portion has a closed end opposite to the mouth.

8. The drainable ostomy pouch according to claim 1, further comprising an evertable pocket wall coupled to at least one of the collection portion and the drain chute, the evertable pocket wall being evertable over at least a portion of the drain chute when the drain chute is in its closed configuration, to cup said portion of the drain chute in a pocket, wherein the pocket is configured to cover all of the folded drain chute when the pocket wall is everted over the drain chute.

9. The drainable ostomy pouch according to claim 8, wherein the evertable pocket wall comprises plural layers of the comfort layer material.

10. The drainable ostomy pouch according to claim 8, wherein the pocket is defined by an exterior face of the pouch, and the evertable pocket wall attached to the exterior of the pouch.

11. The drainable ostomy pouch according to claim 10, wherein the evertable pocket wall is attached to the periphery of the pouch.

\* \* \* \* \*